(12) United States Patent
Van Cappellen et al.

(10) Patent No.: US 8,987,558 B2
(45) Date of Patent: Mar. 24, 2015

(54) CYTOPLASMIC MALE STERILE LEEK PLANTS, METHODS FOR THE PREPARATION AND USE THEREOF, AND A CYTOPLASMIC MALE STERILE GARLIC PLANT

(75) Inventors: Witte Van Cappellen, Alkmaar (NL); Marcel Adriaanse, Haarlem (NL); Eduard Alphonsus Langedijk, Stompetoren (NL); Henricus Chretien Marie Louise Bongers, Baarlo (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 1076 days.

(21) Appl. No.: 13/002,756

(22) PCT Filed: Jul. 14, 2009

(86) PCT No.: PCT/EP2009/058980
§ 371 (c)(1),
(2), (4) Date: Mar. 18, 2011

(87) PCT Pub. No.: WO2010/007059
PCT Pub. Date: Jan. 21, 2010

(65) Prior Publication Data
US 2011/0167509 A1   Jul. 7, 2011

(30) Foreign Application Priority Data
Jul. 14, 2008   (NL) ...................................... 1035698

(51) Int. Cl.
*A01H 5/10* (2006.01)
*A01H 5/12* (2006.01)
(52) U.S. Cl.
CPC ........................................ *A01H 5/12* (2013.01)
USPC ............ 800/298; 800/271; 800/274; 800/303
(58) Field of Classification Search
None
See application file for complete search history.

(56) References Cited

FOREIGN PATENT DOCUMENTS

WO            9847371          4/1998

OTHER PUBLICATIONS

Peterka et al. (Theor. Appl. Genet., (2002), 105, pp. 173-181).*
Yanagino et al. (Theor. Appl. Genet., (2003), 107, pp. 1-5).*
Etoh (J. Japan Soc. Hort. Sci., (1986), 55(3), pp. 312-319).*
Engelke et al., "Mitochondrial genome variation in *Allium ampeloprasum* and its wild relatives" Euphytica 137: 181-194 (2004).
Etoh, T., "Fertility of the Garlic Clones Collected in Soviet Central Asia" J. Japan Soc. Hort. Sci. 55(3): 312-319 (1986).
Peterka et al. "Interspecific hybrids between onion (*Allium cepa* L.) with S-cytoplasm and leek (*Allium ampeloprasum* L)" Theor Appl Genet 94: 383-389 (1997).
Peterka et al., "Transfer of a male-sterility-inducing cytoplasm from onion to leek (*Allium ampeloprasum*)" Theor Appl Genet 105: 173-181 (2002).
Silvertand et al., "Mannelijke steriliteit in prei (*Allium porrum* L.)" Prophyta Misset, Hilversum, NL vol. 43 No. 10 (1989) pp. 289-292; XP008103155.
Yamashita et al., "Seed productivity test of CMS lines of Japanese bunching onion (*Allium fistulosum* L.) possessing the cytoplasm of a wild species, *A. galanthum* Kar. et Kir." Euphytica 136: 327-331 (2004).
Yanagino et al., "Production and characterization of an interspecific hybrid between leek and garlic" Theor Appl. Genet 107: 1-5 (2003).

* cited by examiner

*Primary Examiner* — Brent T Page
*Assistant Examiner* — Jared Shapiro
(74) *Attorney, Agent, or Firm* — Bret E. Field; Bozicevic, Field & Francis LLP

(57) ABSTRACT

The present invention relates to cytoplasmic male sterile leek (*Allium ampeloprasum*) plants comprising cytoplasmic encoded male sterility originating from garlic plant (*Allium sativum* L.) with deposit number NCIMB 41563. Furthermore, the invention relates to a method for providing hereof. And the invention relates to use of the provided plant and of garlic for providing cytoplasmic encoded male sterility.

7 Claims, 4 Drawing Sheets

Figure 1:
Figure 1:

Figure 1: Inflorescence of CMS garlic (A), male fertile garlic (B) and a CMS plant with a leek derived nuclear genome (C).
A
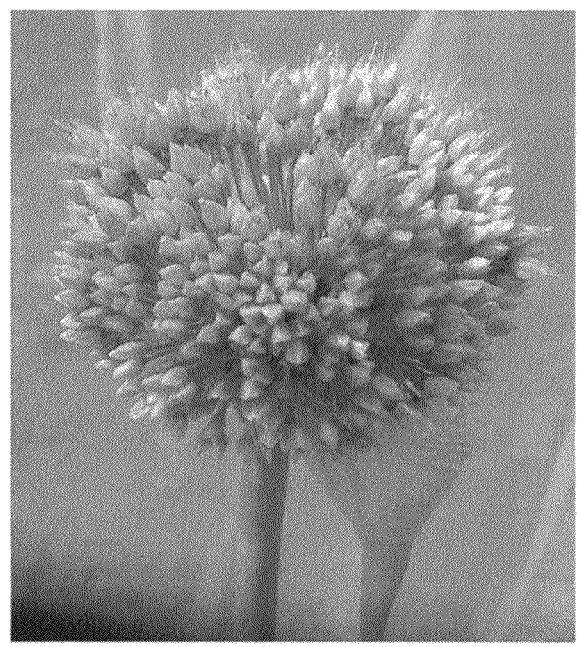

B

C

Figure 2: The restrictionfragment pattern obtained by the PCR-digestion experiment of example 2.

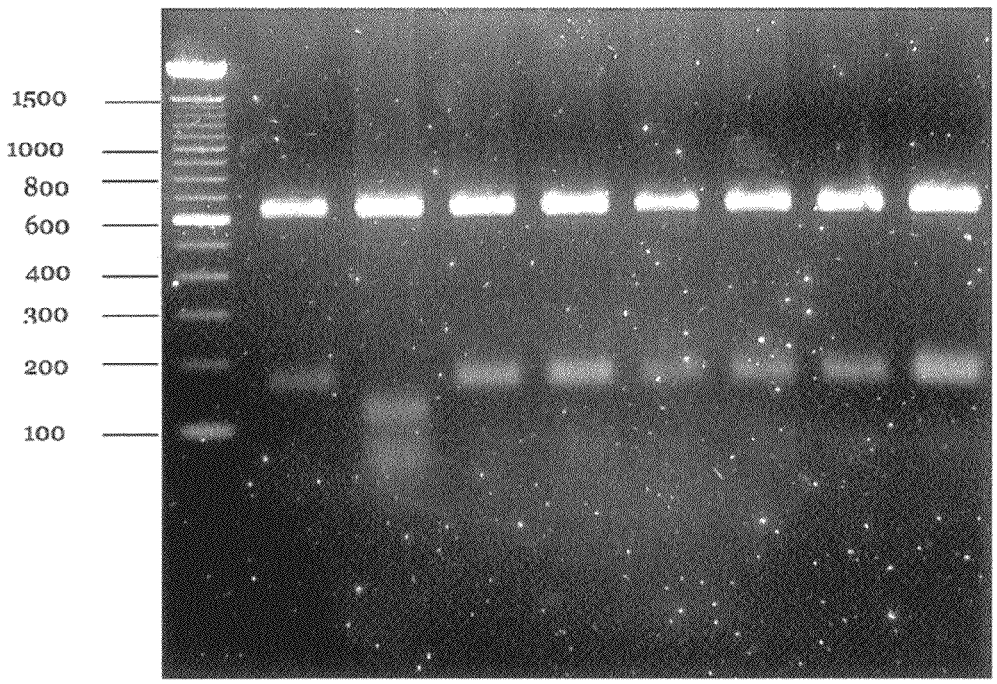

Legend: lane 1: 100 bp ladder (1500 bp - 100 bp)
       lane 2: CMS garlic
       lane 3: fertile leek
       lane 4 - lane 9: CMS garlic - leek cybrids
          4: J18319 (F1 of G18110 as mentioned in example 2)
          5: J18320 (F1 of G18132 as mentioned in example 2)
          6: J18332 (F1 of G18133 as mentioned in example 2)
          7: J18323 (F1 of G18135 as mentioned in example 2)
          8: J18335 (F1 of G18166 as mentioned in example 2)
          9: J18338 (F1 of G18161 as mentioned in example 2)

CYTOPLASMIC MALE STERILE LEEK PLANTS, METHODS FOR THE PREPARATION AND USE THEREOF, AND A CYTOPLASMIC MALE STERILE GARLIC PLANT

The present invention relates to cytoplasmic male sterile, also designated as CMS, leek plants. The present invention additionally relates to methods for producing such cytoplasmic male sterile (CMS) leek (*Allium ampeloprasum*) plants. Further, the present invention relates to a cytoplasmic male sterile (CMS) garlic plant (*Allium sativum* L.). Furthermore, the present invention relates to the use of cytoplasmic male sterile (CMS) leek (*Allium ampeloprasum*) plants or to the use of a cytoplasmic male sterile (CMS) garlic (*Allium sativum* L.) plant for providing cytoplasmic encoded male sterility.

Leek (*Allium porrum* or *Allium ampeloprasum*) belongs to the Alliceae family and is used as a crop in diverse countries. The commercially available leek varieties were open pollinated crossbreds until leek hybrid plants were developed. These leek hybrid plants are plants produced by crossing a selected leek population with another selected leek population. The leek hybrid plants provide advantages over open pollinated crossbreds, such as uniformity, vitality and disease tolerance, resulting in an increased use of leek hybrids in commercial leek productions.

Leek hybrid plants are generally produced by a technique designated in the art as "nuclear male sterility". Nuclear male sterility is a form of male sterility wherein the genetic factor responsible for the observed sterility is encoded by the nuclear genome.

The term "Male sterility" indicates that a plant has no fertile pollen and, because of this, the male sterile plant is incapable of self pollination.

As a result of nuclear genome encoded male sterility, this type of plant sterility is only inherited by some of the progeny. Consequently, in order to maintain the nuclear male sterility characteristics, vegetative propagation of a nuclear male sterile parent line is often required.

An example of vegetative propagation to circumvent the above partial loss of sterility in the progeny is propagation by tissue culture. A drawback of tissue culturing vegetative propagation is that the method is time consuming and expensive. Other forms of vegetative propagation, such as the production of young plants on the capitulum, result in a serious risk for developmental disorders and the spread of diseases and infections, e.g., infections caused by viruses.

Considering, amongst others, the above indicated disadvantage associated with vegetative propagation, the use of nuclear male sterility is suffering from serious drawbacks regarding the use thereof for the production, or propagation, of leek hybrid plants.

Another form of male sterility is cytoplasmic encoded male sterility (CMS). In line with the general meaning in the field of plant production, cytoplasmic encoded male sterility indicates that the observed characteristic, or phenotypic trait, in plants that no fertile pollen are formed, resulting in that these plants are not capable of self pollination, is genetically encoded in the cytoplasm, in most cases by mitochondrial, and is some cases by chloroplast, DNA. Cytoplasmic encoded male sterility is inherited via the female line, i.e., cytoplasmic encoded male sterility is transferred through the cytoplasm of an egg cell to the progeny. It is possible to restore the fertility of progeny using Rf (restoration or fertility) genes. Since these Rf genes inherit in a Mendelian fashion, in contrast with the coding genetic material in the cytoplasm which is only inherited through the female line, it is likely that these Rf genes are encoded by the nuclear genome.

Cytoplasmic encoded male sterility appears to be a suitable, and advantageous, alternative for the production of leek hybrid plants. This, amongst others, because of the possibility to maintain, without any further measures, the property in the progeny.

Accordingly, it is an object, amongst other objects, of the present invention, to provide cytoplasmic male sterile leek (*Allium ampeloprasum*) plants. This object, amongst other objects, is met by the present invention through a method as defined in the appended claim 1.

Specifically, this object, amongst other objects, is met by the present invention by providing a cytoplasmic male sterile (CMS) leek (*Allium ampeloprasum*) plant comprising cytoplasmic encoded male sterility originating from garlic plant (*Allium sativum* L.) with deposit number NCIMB 41563.

In their search for providing cytoplasmic male sterile leek (*Allium ampeloprasum*) the inventors followed an unconventional route. Specifically, they started to identify forms of cytoplasmic encoded male sterility in a plant wherein forms of cytoplasmic encoded male sterility were unknown, or not observed. This resulted in the identification of cytoplasmic male sterility in garlic (*Allium sativum* L).

Specifically, by using techniques as disclosed in WO9847371, the inventors intensified their study of garlic's pollen fertility. This enabled the inventors for a focused search for male sterility in garlic. Particularly, the inventors were successful in developing garlic plants with a male sterile inflorescence, while maintaining their female fertility. After studying the heredity, i.e., the inheritance of the observed sterility, it was shown that this male sterility inherits via the female line, which is indicative of a form of cytoplasmic encoded male sterility.

The inventors deposited a cytoplasmic male sterile garlic plant (*Allium sativum* L.) at the NCIMB in Aberdeen, Scotland, UK, with deposit number NCIMB 41563.

According to a preferred embodiment, the cytoplasmic encoded male sterily (CMS) of the present leek (*Allium ampeloprasum*) plants is mitochondrial encoded male sterility. The term mitochondrial encoded indicates that the genetic factor providing male sterility is found in the mitochondria.

According to a further preferred embodiment, the present cytoplasmic male sterile (CMS) leek (*Allium ampeloprasum*) plants comprises mitochondria of a garlic plant (*Allium sativum* L.) with deposit number NCIMB 41563 encoding cytoplasmic male sterility. Accordingly, the specific garlic (*Allium sativum* L.) with deposit number NCIMB 41563 is also designated herein as the donor of cytoplasmic encoded male sterility.

According to another further preferred embodiment, the present cytoplasmic male sterile (CMS) leek (*Allium ampeloprasum*) plant, is a leek plant with deposit number NCIMB 41556. The inventors deposited this specific leek plant at the NCIMB in Aberdeen, Scotland, UK, with deposit number NCIMB 41556, or plant from which the cytoplasmic male sterility originates.

The present invention, according to a further aspect, relates to the seeds, pollen, parts of mature plants, parts of embryonic plants or cells, of the present cytoplasmic male sterile (CMS) leek (*Allium ampeloprasum*) plants.

Non limiting, but preferred, examples of parts of mature plants can be a leaflet, blade, ovary, filament, style, stigma, petiole, lateral bud, stem, cotyledon, hypocotyl, flower, branch root or primary root.

Non limiting, but preferred, examples of embryonic plants or cells can be a radicle, hypocotyl, epicotyl, bulb, bulbils, fibrous root, leaflet or tunic.

According to a further aspect, the present invention relates to a cytoplasmic male sterile (CMS) garlic plant (*Allium sativum* L.) with deposit number NCIMB 41563.

Such a cytoplasmic male sterile garlic plant can be obtained by selection of plants from a population garlic plants with an improved inflorescence according to the method as disclosed in WO9847371. Example 1 below discloses a more detailed description for obtaining a garlic plant with cytoplasmic male sterility, or CMS. Seeds from plants with CMS are deposited at the NCIMB, Aberdeen, Scotland, UK under number 41563.

According to a further aspect, the present invention relates to the seeds, pollen, parts of mature plants, parts of embryonic plants or cells, of a garlic plant (*Allium sativum* L.) with deposit number NCIMB 41563.

Non limiting, but preferred, examples of parts of mature plants can be a leaflet, blade, ovary, filament, style, stigma, petiole, lateral bud, stem, cotyledon, hypocotyl, flower, branch root or primary root.

Non limiting, but preferred, examples of embryonic plants or cells can be a radicle, hypocotyl, epicotyl, bulb, bulbils, fibrous root, leaflet or tunic.

According to a further aspect, the present invention relates to use of the present cytoplasmic male sterile (CMS) leek (*Allium ampeloprasum*) plant for providing cytoplasmic encoded male sterility. Further, the present invention relates to the use of garlic plant (*Allium sativum* L.) with deposit number NCIMB 41563 for providing cytoplasmic encoded male sterility. Furthermore, the present invention relates to the use of the seeds, pollen, parts of mature plants, parts of embryonic plants or cells from said leek and said garlic for providing cytoplasmic encoded male sterility.

The invention, according to yet a further aspect, relates to use of a garlic plant (*Allium sativum* L.) for providing cytoplasmic encoded male sterility in a plant, preferably a leek (*Allium ampeloprasum*) plant.

According to a preferred embodiment, a garlic plant is used for providing cytoplasmic encoded male sterility in a plant chosen of the genus *Allium*, for instance leek (*Allium ampeloprasum*), onion (*A. cepa* L.), chive (*A. schoenoprasum*), ramsons (*A. ursinum*), Chinese chive (*A. tuberosum* Rottier) or (*Allium sativum* L.).

According to another preferred embodiment, the present garlic plant is a cytoplasmic male sterile garlic plant.

The present invention, according to still a further aspect, relates to methods for producing a cytoplasmic male sterile (CMS) leek (*Allium ampeloprasum*) plant, comprising cytoplasmic encoded male sterility originating from garlic (*Allium sativum* L.) with deposit number NCIMB 41563, comprising the steps of:

(i) crossing a leek (*Allium ampeloprasum*) plant with a garlic (*Allium sativum* L.) plant wherein said garlic (*Allium sativum* L.) plant originates from, or is, garlic (*Allium sativum* L.) with deposit number NCIMB 41563 for providing a population F1 plants comprising cytoplasmic encoded male sterility;

(ii) backcrossing a cytoplasmic male sterile F1 plant obtained in step (i) with a leek (*Allium ampeloprasum*) plant, preferably the leek plant of step (i), for providing a population backcrossed cytoplasmic male sterile $BC_1$ plants;

(iii) optionally, backcrossing one or more times a $BC_1$ plant obtained in step (ii) with a leek (*Allium ampeloprasum*) plant, preferably the leek plant of step (i), for providing a subsequent population backcrossed cytoplasmic male sterile $BC_n$ plants.

In the method according to the present invention, a cytoplasmic male sterile garlic plant is combined as a mitochondrial donor with a male fertile leek plant. A garlic (*Allium sativum* L.) plant which originates from, or is, garlic (*Allium sativum* L.) with deposit number NCIMB 41563, can be considered as seed stock (or intermediary) for providing CMS the plants according to the present invention.

The first crossing results in the development of garlic-leek cybrids comprising cytoplasmic encoded male sterility forming a population F1 plants. These cybrids provide fore a route for the successful development of the present leek plants. Plants of the F1 population can be tested for the presence of CMS by studying their capacity for self-pollination and by determining whether the observed male sterility is transferred through the female line, i.e., the cytoplasm.

Generally, cells from the obtained F1 plants according to step (i) will have a nuclear genome which can be regarded as an intermediary genome between garlic and leek, i.e., these plant comprise nuclear genome originating from both leek and garlic. Because of the use of garlic as the female donor, inherently, the cytoplasm, and more particularly the mitochondria and chloroplasts, are derived from the female garlic donor plant. In order to provide leek plants, i.e., plants substantially comprising leek nuclear DNA, the cytoplasmic male sterile F1 plants according to step (i), are backcrossed with leek plants (step (ii)), preferably, the present leek male donor, until leek plants are provided.

Backcrossing of cytoplasmic male sterile $BC_1$ plants, i.e., the first backcross plants, with a fertile leek plant can continue over a couple of generations, preferable successive generations, in order to increase the amount of the genomic material of the leek plant in the nuclear genome of the line BC plants.

Preferably this backcrossing is continued over a number of generations (for example $BC_2$ to $BC_n$) of the BC line. Generally, in each backcrossing, the amount of the garlic leek genomic material will halve. In this way the use backcrossings provides a plant wherein the nuclear genome comprises substantially nuclear genetic material of leek. Such a plant is regarded in the art as a leek plant, i.e., providing all phenotypical traits generally associated in the art with leek plants and nuclear encoded.

Plants with a nuclear genome of leek which is at least 95%, preferably 98%, more preferably 99%, and most preferably substantially 100%, further comprising the present cytoplasmic encoded male sterility, are preferred and suitable for obtaining other leek plants with cytoplasmic encoded male sterility properties.

According to a preferred embodiment, the present method for producing a cytoplasmic male sterile (CMS) leek (*Allium ampeloprasum*) plants, comprises selecting cytoplasmic male sterile plants comprising mitochondria encoding cytoplasmic male sterility originating from NCIMB 41563 using DNA analysis.

According to a preferred embodiment, DNA analysis is based on analyzing mitochondrial DNA, for example mitochondrial specific probes which are specific for garlic cytoplasm and are therefore linked to the cytoplasmic encoded male sterility property.

According to another preferred embodiment, DNA analysis is based on analyzing nuclear DNA. For example, crossbred BC plants with an increased share of leek genomic material can be selected from the BC progeny. It was observed that the elimination of the garlic genetic material succeeds faster than is expected on the theoretical mutual distribution of chromosomes.

After each generation, flowcytometry, by measuring the relative DNA quantity, is used to determine to what extent the obtained hybrid plants comprised an intermediary garlic-leek genome. Surprisingly, it was shown that some plants comprised no measurable quantity of garlic genome after two generations of backcrossing, thus, within the experimental error of this type measuring, these plants comprised substantially 100% of nuclear DNA originating from leek.

According to another embodiment, the present method for producing a cytoplasmic male sterile (CMS) leek (*Allium ampeloprasum*) plants further comprises a hormone treatment for influencing the flowering time of present leek (*Allium ampeloprasum*) and/or present garlic (*Allium sativum* L.) plants.

As is known in the art, techniques such as embryo-rescue or others techniques such as in vitro germination or hormone treatment to influencing the flowering time of plants can offer advantages for crossing plants of different species. In several cases, the use of these techniques can be necessary.

A method according to the invention results in a plant with a nuclear leek genome, comprising cytoplasmic encoded male sterility (CMS) originating from garlic (*Allium sativum* L.) with deposit number NCIMB 41563.

The invention is further elucidated in the following non-limiting examples of preferred embodiments. In the examples, reference is made to the appended figures wherein:

FIG. 1: shows photographs of A: the inflorescence of a cytoplasmic sterile garlic plant of the invention, B: the inflorescence of a male fertile garlic and C: the inflorescence of a cytoplasm sterile plant of the invention with a leek derived nuclear genome.

FIG. 2: shows a restriction fragment pattern obtainable from the PCR digestion experiment of the below example 2.

EXAMPLE 1

By application of the invention disclosed in WO9847371 garlic plants are obtained which showed a fertile flowering. With a fertile flowering is understood to mean the partially or complete absence of bulbils in the inflorescence of this garlic. At the same time the present flowers are developed good and complete.

Treatment of garlic plants in a way as disclosed by this patent led to a first in-depth study on the inflorescence of garlic.

Surprisingly, some garlic plants were selectable in which a non Mendelian descending form of male sterility (CMS) was determined. It was determined that these plants none pollen formed and that this property inherits to the following generation via the egg cells for 100%. If there was a Mendelian descending than 50% of the next generation supposed to contain the property.

The inflorescence of a CMS garlic plant is shown in FIG. 1A. In comparison of this inflorescence with the inflorescence of a male fertile garlic plant, as is shown in FIG. 1B, it became clear that in the inflorescence of FIG. 1A none pollen carrying stamen are present.

EXAMPLE 2

Six CMS garlic lines, characterized by the number G18110, G18132, G18133, G18135. G18161 and G18166, were jointly flowered with a broad spectrum of leek lines in order to increase pollination turns. This spectrum was chosen in such a way that the flowering of the leek pollinator was as long as possible.

On these six lines asymmetric fructification is determined in different extents. And in vitro germination is applied, preferably within 6-8 weeks after pollination.

If the developing embryos were not removed and put up a degeneration of the endosperm takes place. This phenomenon is clearly described by for example Sharma et al. and does not lead to the further development of viable seed. This technique was applied if the typical asymmetric fructification was clearly visual by the unaided eye. Put up of an ovary, from the color light brown till black, took place at a B5 medium (Gamborg et al.), which is an often used medium for the technique of in vitro germination.

It turned out to be essential for the use of this technique that the flowering delay of leek and the flowering stimulation of garlic was influenced by treatments that influence the flowering time. Examples are hormone treatments, variation in temperature and in the length of a day.

In this specific case, a hundred different ovary, in different stadia of development, were putted up. 43 Individual plants arised.

By application of the flowcytometry (Partec, Münster, Germany) relative DNA quantities of the developed material were measured. By application of this technique is determined:

27 plants had the expected intermediary pattern between garlic and leek,
14 plants escaped (garlic FCM pattern)
2 plants exhibited a deviate pattern.

From all plant is a cytoplasm of the CMS garlic type determined. For this purpose the following primers were used:

p12351:  5'-ACC AGA AGG ATT CGG ATT GA-3' p12352:  5'-TGA CAT AAG TCC CTC CCT ACA A-3'

| Conditions for the PCR were: | |
|---|---|
| DNA | 2 µl |
| buffer 10 x | 2.5 µl |
| 50 mM MgCl$_2$ | 1.2 µl |
| NTP's | 0.6 µl |
| p12351 (5 pM) | 1 µl P12351 |
| p12352 (5 pM) | 1 µl P12352 |
| H$_2$O | 16.6 µl |
| Platinum Taq | 0.1 µl |

| Programm SA59: | | |
|---|---|---|
| stap | | |
| 1 | 94° C. | 5 minutes |
| 2 | 60° C. | 1 minutes |
| 3 | 72° C. | 1 minutes |
| 4 | 94° C. | 30 seconds |
| 5 | 59° C. | 1 minutes |
| 6 | 72° C. | 1 minutes |
| 7 | Go to step 4 29 times | |
| 8 | 72° C. | 5 minutes |
| 9 | 20° C. | 20 minutes |

Amplification of a fragment by means of these primers gave in both garlic and leek a fragment of 845 bp.

After digestion of this fragment by the restriction enzyme Taq1 CMS garlic provided three fragments of 60 bp, 160 bp and 625 bp respectively, while leek provided four fragments of 50 bp, 60 bp, 110 bp, and 625 bp respectively.

FIG. 2 shows the restriction fragment band pattern on an electrophoresis gel belonging to this experiment. The most distinctive difference between the pattern of garlic and leek are the streams of 110 bp and of 160 bp. This stream of 110 bp is present in the leek pattern and absent in the CMS garlic pattern. Oppositely, the stream of 160 bp is present in CMS garlic pattern while absent in the leek pattern. With the help of the presence of the 160 bp stream and the absence of the 110 bp stream, the corresponding cytoplasm of the CMS garlic-leek cybrids in the lanes 4-9 to the CMS garlic cytoplasm, could be determined.

The described crossing between garlic (2n=2x=16) and leek (2n=4x=32) resulted in plants which are triploid in a certain way (2n=3x=24); such plants are practically always male and female sterile because the meiosis fails. In order to prove that there is male sterility, a part of the developed plants is further developed to a 4n (=6x=48) plant.

A common applied chromosome doubling technique, in this field of study, is used by means of a colchicine treatment. Hereto, meristems were placed for 3-6 days on a colchicine based conservation medium B5 (completed with 35 mg colchicine/l). Afterwards a further grow into a complete plant took place on a B5 medium without additives.

These plans are studied of their inflorescence in the second season.

As a conclusion after a visual examination, as well as examination by pollen coloring and pollen germination techniques, is determined that all developed crossing products male sterile were. Even the above mentioned 4n (=6x=48) plants turned out to be incapable in self-pollination.

Therewith is proven the transfer of the CMS cytoplasm, developed after hormone treatment in garlic, with maintenance of functionality, to leek.

Via a further crossing with leek turned it out to be possible to obtain progeny for each of the six garlic CMS lines; herein is, once again, the above described method of in vitro germination applied.

Measurements in these crossings products by flowcytometrie are performed, however as a result of increased hybridization of genomes move the peaks of the cytograms to each other. Through this the technique of flowcytometrie is no longer distinctive after several backcrossings. Because of this there was chosen for a global division of the progeny in groups.

Up here, the following division was used;
Group 1: expected flowcytogram with a BC 1 pattern (backcrossing 1)
Group 2: flowcytogram measured after duplication of nuclear material.
Group 3: parent plant FCM pattern (wherein mother tissue is propagated instead of isolated outgrown embryo).
Group 4: deviated FCM patterns.

In the first group of 'expected BC 1 pattern', a new crossing with leek (BC2=backcrossing 2) turned out to be possible, although with the difference that the maturation of seed took place at the plant. This is a major step forward in the development of the product because in vitro germination blocks a commercial use of the invention in the practical application of seed-cultivation.

This 'natural' crossing with leek established with the present invention already in the BC2 phase. However, in some cases this crossing established in the BC3, BC4 or even in later generations.

EXAMPLE 3

Additionally, it turned out to be possible to develop a 4n (6x) plant directly from the set of developed F1 in vitro germinated plants between garlic and leek, contrary to the above mentioned '3x' plants. Surprisingly, a spontaneous doubling of the chromosomes occurred in the garlic egg cell, which results in a 2n gamete. This results in a tetraploid progeny after crossing with leek (2n pollen).

The appearance of unreduced gametes is described in the literature (Ramsey and Schemske).

The work of Peterka et al. disclosed that an unreduced gamete of onion causes this, for an obtained backcrossing between leek and onion.

This 4n plant is identified by flowcytometrie and is compatible with leek.

As a result of that, the setting of seeds occurred spontaneously, which by means of in vitro germination could grow up to mature plants. Germination occurred at 15° C. by darkness.

EXAMPLE 4

The fourth possibility comprises the crossing, via the intermediary step of making a tetraploid garlic, with leek. Herewith, the genetic compilation of both plants species is both tetraploid, which accelerates the fuse of gametes in a viable combination.

However, the development of CMS garlic lines followed by above mentioned techniques remains necessary here.

The invention claimed is:

1. A cytoplasmic male sterile (CMS) leek (*Allium ampeloprasum*) plant comprising cytoplasmic encoded male sterility originating from garlic plant (*Allium sativum* L.) with deposit number NCIMB 41563.

2. The cytoplasmic male sterile (CMS) leek (*Allium ampeloprasum*) plant according to claim 1, wherein said cytoplasmic encoded male sterility is mitochondrial encoded male sterility.

3. The cytoplasmic male sterile (CMS) leek (*Allium ampeloprasum*) plant according to claim 1, comprising mitochondria of garlic plant (*Allium sativum* L.) with deposit number NCIMB 41563 encoding cytoplasmic male sterility.

4. The cytoplasmic male sterile (CMS) leek (*Allium ampeloprasum*) plant according to claim 1, wherein said leek is a leek plant with deposit number NCIMB 41556.

5. Seeds, parts of mature plants, parts of embryonic plants or cells, of a cytoplasmic male sterile (CMS) leek (*Allium ampeloprasum*) according to claim 1, wherein said parts or cells comprise cytoplasmic male sterility originating from garlic plant (*Allium sativum* L.) with deposit number NCIMB 41563.

6. A cytoplasmic male sterile (CMS) garlic plant (*Allium sativum* L.) with deposit number NCIMB 41563.

7. Seeds, parts of mature plants, parts of embryonic plants or cells, of a cytoplasmic male sterile (CMS) leek (*Allium ampeloprasum*) according to claim 6, wherein said parts or cells comprise cytoplasmic male sterility originating from garlic plant (*Allium sativum* L.) with deposit number NCIMB 41563.

* * * * *